United States Patent [19]

Sjostrom

[11] Patent Number: 4,983,179

[45] Date of Patent: * Jan. 8, 1991

[54] ARTHROSCOPIC SURGICAL INSTRUMENT

[75] Inventor: Douglas D. Sjostrom, Wakefield, Mass.

[73] Assignee: Smith & Nephew Dyonics Inc., Andover, Mass.

[*] Notice: The portion of the term of this patent subsequent to May 30, 2006 has been disclaimed.

[21] Appl. No.: 320,628

[22] Filed: Mar. 8, 1989

Related U.S. Application Data

[63] Continuation of Ser. No. 948,315, Dec. 30, 1986, Pat. No. 4,834,729.

[51] Int. Cl.$^5$ .............................................. A61B 17/32
[52] U.S. Cl. ..................................... 606/180; 609/22; 606/170
[58] Field of Search .................. 604/22; 128/305, 318; 606/167-173, 159, 180

[56] References Cited

U.S. PATENT DOCUMENTS

| | | |
|---|---|---|
| 1,867,624 | 7/1932 | Hoffman . |
| 3,618,611 | 11/1971 | Urban . |
| 3,990,453 | 11/1976 | Douvas et al. . |
| 3,995,619 | 12/1976 | Glatzer . |
| 4,018,228 | 4/1977 | Goosen . |
| 4,111,207 | 9/1978 | Seiler, Jr. . |
| 4,203,444 | 5/1980 | Bonnell et al. . |
| 4,239,045 | 12/1980 | Schlein . |
| 4,258,716 | 3/1981 | Sutherland . |
| 4,274,414 | 6/1981 | Johnson et al. . |
| 4,461,305 | 7/1984 | Cibley . |
| 4,513,745 | 4/1985 | Amoils . |
| 4,543,857 | 10/1985 | Kleinberg et al. . |
| 4,572,181 | 2/1986 | Mattler . |
| 4,579,118 | 4/1986 | Failla . |
| 4,586,497 | 5/1986 | Dapra et al. . |
| 4,589,414 | 5/1986 | Yoshida et al. . |
| 4,598,710 | 7/1986 | Kleinberg et al. . |
| 4,649,919 | 3/1987 | Thimsen et al. . |
| 4,672,965 | 6/1987 | Baum . |
| 4,834,729 | 5/1989 | Sjostrom . |

OTHER PUBLICATIONS

EPC Applicant No. 0,190,000, published Aug. 6, 1986.
Chirurgie-Katalog 20, Martin, pp. 30, 33, 38, 188-189.
"Optical Bronchoscopy Forceps", Wolf, p. 620A.
Surgical Instrument Catalog, Storz Instrument Company (1966), pp. 146, 213, 215, 240.
Concept Incorporated (8 pages).
Fine Surgical Instruments, Amico GmbH (1966), pp. 37-41, 207, 334, 378-379.
"Basket Forceps", Dyonics, Inc. (7/1/86).
Commercial Literature of Chattanooga Corporation for "DEXTRA" Precision Power System.
Commercial Literature of SHUTT Medical Technologies Incorporated.

Primary Examiner—John D. Yasko
Assistant Examiner—Kathleen A. Daley
Attorney, Agent, or Firm—Fish & Richardson

[57] ABSTRACT

An arthroscopic surgical instrument consists of an outer stationary member having a distal aperture, the wall of the outer member defining a first cutting edge at the aperture; an internal movable member disposed within the outer member, adapted to be power driven and having a second cutting edge arranged to move toward and closely past the first cutting edge in rapid, repetitive fashion to sever tissue. The instrument further includes a table extension provided at the aperture, projecting outwardly from the general contour of the body of the outer stationary member. The table extension is constructed and arranged to engage tissue against which the operator urges the instrument, in a manner to improve the repetitive cutting action. In one embodiment, the internal movable member disposed within the outer member has at least a pair of second cutting edges arranged to move sequentially toward and closely past fixed cutting edge to sever tissue at a shearing point, each second cutting edge defining one or more cutting points arranged longitudinally along the second cutting edge, and a cutting point of one second cutting edge being offset longitudinally from a cutting point of the next following second cutting edge, whereby the sequential second cutting edges have different cutting patterns.

15 Claims, 8 Drawing Sheets

ARTHROSCOPIC SURGICAL INSTRUMENT

This is a division of application Ser. No. 948,315 filed Dec. 30, 1986, issued as U.S. Pat. No. 4,834,729 on May 30, 1989.

BACKGROUND OF THE INVENTION

This invention concerns improved arthroscopic surgical instruments.

The effective use of powered instruments for arthroscopically cutting and shaping tissues within a joint dates from an invention which I helped create (U.S. Pat. No. 4,203,444, issued May 20, 1980). Such instruments are now in wide use. As skills have advanced, surgeons have desired more aggressive and faster acting instruments, and instruments suitable for an expanded range of tasks. Prior individual instruments, however, have usually been suited for only one or a rather limited number of functions because of the differences in tissue to be removed. These tissues vary from hard to soft, firmly attached to very mobile, and easy to approach to difficult and awkward of access.

Not only is the changing of instruments time consuming, but also each change increases the probability of scuffing or otherwise injuring healthy tissue as the various arthroscopic instruments are slid in and out of the joint. The present invention provides an arthroscopic instrument capable of removal of a wide variety of tissues. This not only decreases the risk of inadvertent scuffing, etc., but also increases the speed of the procedure. This swiftness can avoid physician fatigue, minimize anesthesia time for the patient, and increase the number of procedures possible with a given operating room facility.

The invention, in common with prior powered instruments, employs an outer stationary member sized to enter the joint through a puncture opening. The outer member has at least one distal aperture at which the wall of the outer member defines a first, fixed blade surface terminating in a cutting edge. An internal movable member, disposed within the outer member and adapted to be power driven, has a second cutting edge arranged to move toward and closely past the fixed cutting edge in rapid, repetitive fashion to sever tissue. The movable member has an associated drive means which repeatedly moves the second cutting edge in this cutting direction.

According to one aspect of the present invention, an improvement lies in the provision of a table extension at the aperture, projecting outwardly from the general contour of the body of the outer stationary member, the extension constructed and arranged to engage tissue against which the operator urges the instrument, in a manner to improve the repetitive cutting action.

In preferred embodiments of the invention, the table extension projects in retrograde manner with an outward component and a component of projection in the direction opposite to the direction of cutting movement of the inner member; the aperture is provided in the side wall of the outer member, and the table extension projects outwardly beyond the general outer side surface of the outer member in the vicinity of the aperture, preferably a blade surface that corresponds to the thickness of the side wall of the outer member lies at a retrograde angle to a radius from the axis of movement of the inner member projected through the first cutting edge and the table extension lies at a greater angle to the radius, and preferably the table extension projects outward from the general contour of the outer surface of the outer member by at least 20% of the thickness of the general side wall of the outer member; the table extension projects outward by at least the order of the thickness of the general side wall, preferably the table extension projects from the blade surface by at least the order of the thickness of the general side wall of the outer member; the table extension projects in a retrograde manner from the blade surface by at least 20% of the thickness of the general side wall of the outer member, preferably the table extension projects from the blade surface by at least the order of the thickness of the general side wall of the outer member; the instrument includes a notch provided in the region of intersection between the proximal end of the table extension and the general side wall of the outer member; the outer member is generally circular in transverse cross section and is tapered distally in a region proximal of the aperture; the outer member at opposite sides of the aperture defines a pair of first, fixed cutting edges, the movable member adapted to move selectively in opposite directions and defining a pair of second cutting edges each adapted to coact with a respective cutting edge of the first pair, and there being a table extension associated with each fixed cutting edges, preferably the inner cutter has two cutting edges that provide cutting points arranged in a different pattern so that points on one edge are staggered longitudinally from any point on the other edge, preferably each table extension surface extends outwardly to at least a line projected tangent to the path of a second cutting edge at its midpoint between first cutting edges, and preferably the table extension has an outer surface disposed generally on or within a line projected tangent to outer surface of the outer member at the radius of the path of travel of the second cutting edge at 90° after the midpoint; the cutter defines two apertures, and comprises at least one table extension at each aperture; the outer member comprises a tube having a generally cylindrical form; the table extension defines a tissue surface; and the outer member comprises a tube having a generally cylindrical form, the aperture is provided in the side wall of the tube, and the table extension projects outwardly beyond the cylinder projected through the outer surface of the tube in the vicinity of the aperture, the outer member at opposite sides of the aperture defines a pair of first, fixed cutting edges, the first fixed edges extending generally parallel to the axis of the tube, the movable member adapted to move selectively in opposite directions and defining a pair of second cutting edges each adapted to coact with a respective cutting edge of the first pair, and there being a table extension associated with each fixed cutting edge, each of the table extensions projecting generally outwardly from the edge surface with a component of extension in the direction opposed to the direction of cutting movement of the inner member, preferably a line projected between outermost tips of the pair of table extensions lies substantially tangent to the path of travel of the inner cutting edges, preferably the tube has a diameter of 5 millimeters or less and the table extension projects outward from the general contour of the outer surface of the tube by at least 20% of the thickness of the general side wall of the tube, and preferably the table extension defines a tissue immobilizing surface.

According to another aspect of the invention, an arthroscopic surgical instrument instrument comprises an outer stationary member sized to enter a joint through a puncture opening and having a distal aperture, the wall of the outer member at the aperture defining a first, fixed cutting edge, an internal movable member disposed within the outer member, the movable member having at least a pair of second cutting edges arranged to move sequentially toward and closely past the fixed cutting edge to sever tissue at a shearing point and adapted to be power driven for repeated, rapid movement of the second cutting edges in the cutting direction, each second cutting edge defining one or more cutting points arranged longitudinally along the second cutting edge, and a cutting point of one second cutting edge being offset longitudinally from a cutting Point of the next following second cutting edge, whereby the sequential second cutting edges have different cutting patterns.

In preferred embodiments of this aspect of the invention, the outer member at opposite sides of the aperture defines a pair of first, fixed cutting edges, the movable member adapted to move selectively in opposite directions and defining pairs of second cutting edges, each pair of second cutting edges adapted to coact with a respective first cutting edge; and, due to assymetric arrangement of the cutting points, the body of the inner member, in the area of the second cutting edges, is of substantially uniform axial section.

There is thus provided an instrument capable, in a majority of instances, of performing an entire arthroscopic surgical procedure, including, e.g., articular cartilage resections and meniscectomies, normally performed in the past debridement, synovial resection, removal of osteophytes, plica only by use of multiple instruments, with attendant increase in time, trauma, and risk of injury to healthy tissue in the joint.

These and other features and advantages of the invention will be apparent from the following description of the preferred embodiment, and from the claims.

PREFERRED EMBODIMENT

We first briefly describe the drawings.

DRAWINGS

FIG. 1 is a much enlarged, somewhat diagrammatic, transverse section of the outer member of the surgical instrument of the invention, taken across the distal aperture, with the inner member shown in dashed line, while

FIG. 4 is a plan view of the distal end portion of the outer stationary member of the instrument, while

FIG. 7 is a top plan view of the inner, rotatable member of the surgical instrument of the invention, while

STRUCTURE

Figure 1:
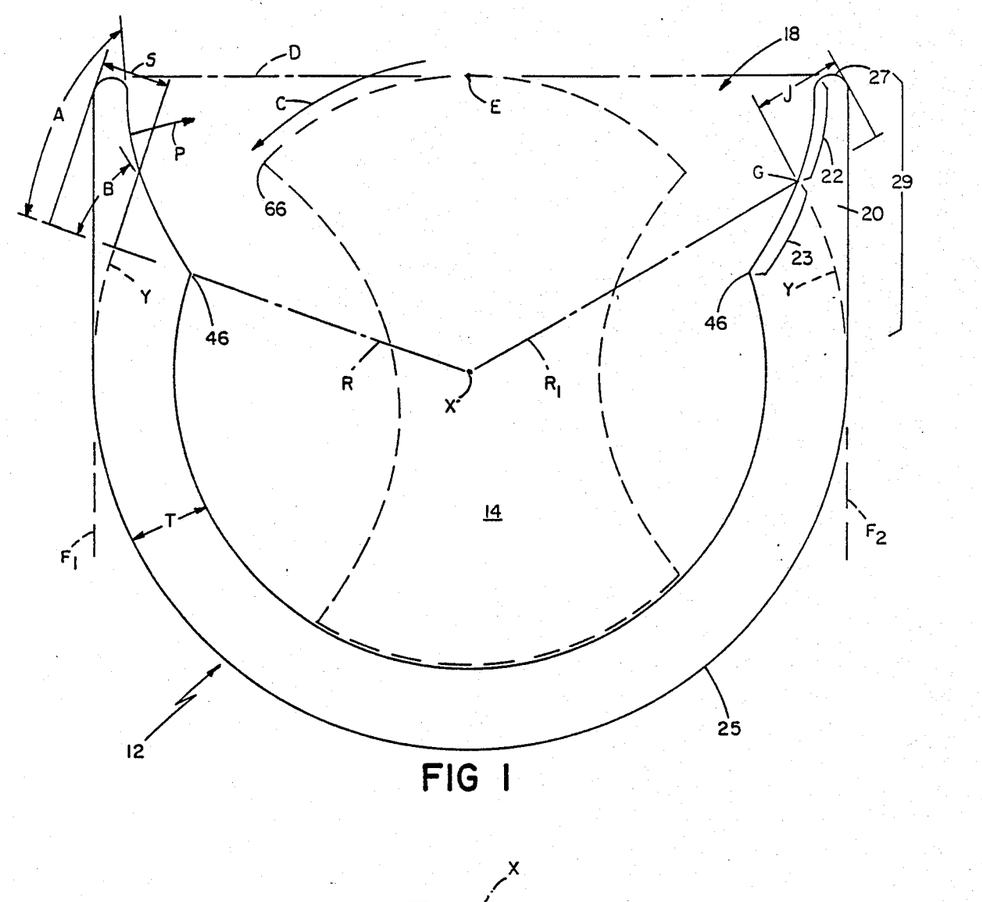
Figure 2:
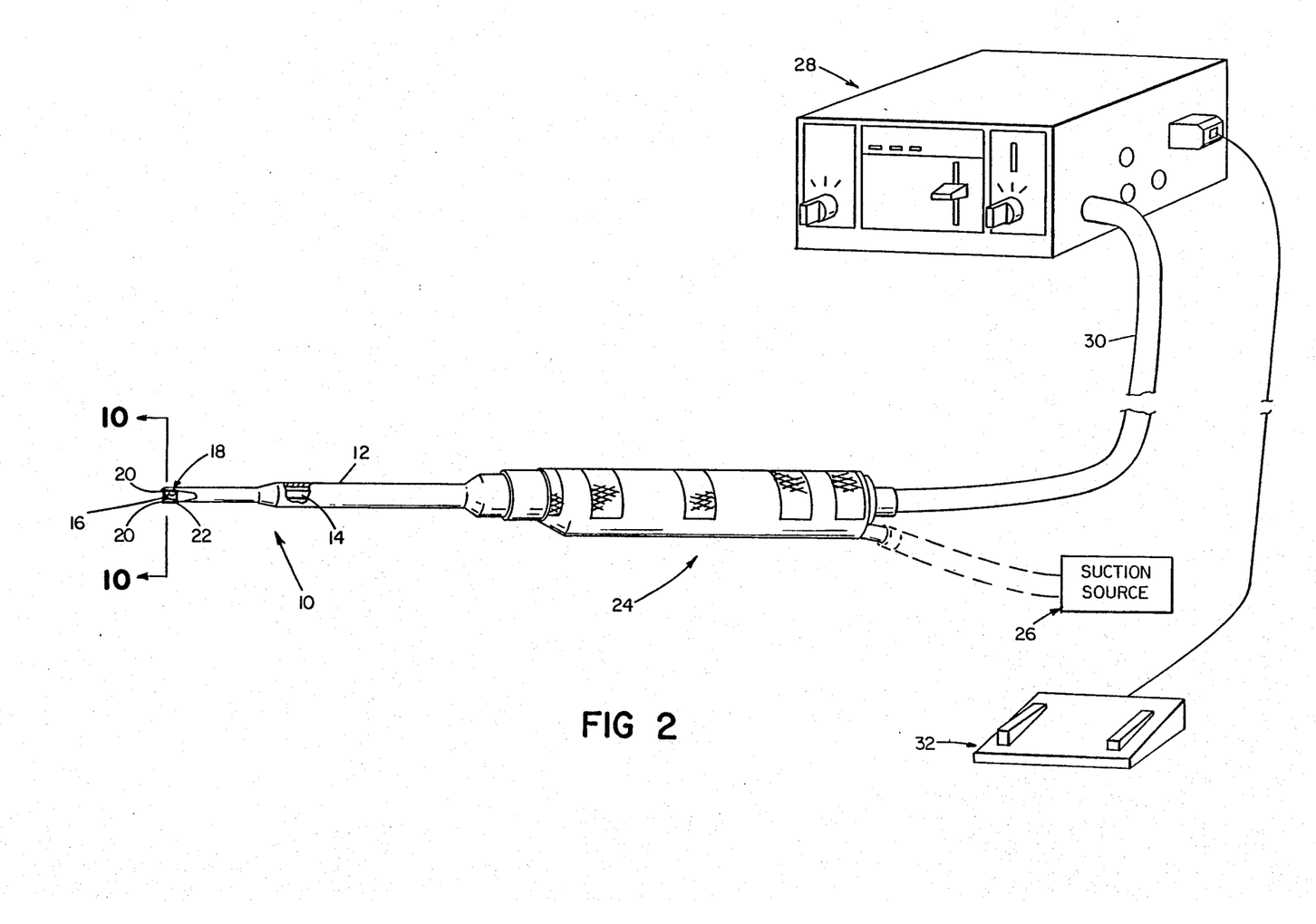
FIG. 2 is a perspective view, partially in section, of the arthroscopic surgical instrument of the invention with a Power unit and handpiece.
Figure 3:
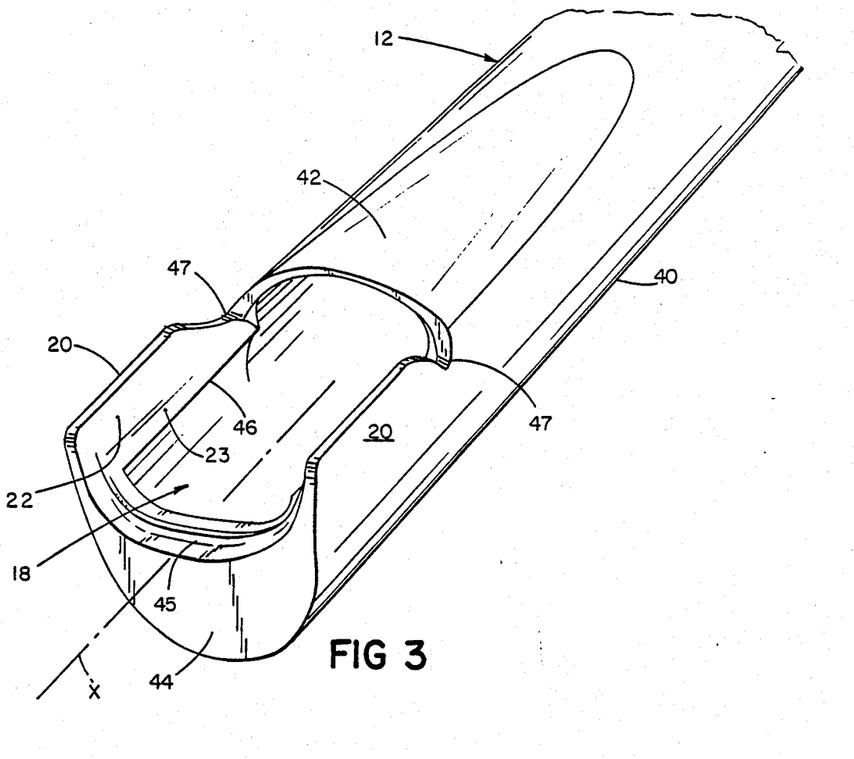
FIG. 3 is an enlarged perspective of the distal portion of the outer stationary member of the instrument of FIGS. 1 and 2.

Referring to FIGS. 1, 2 and 3, the powered arthoscopic surgical instrument 10 of the invention consists of an outer stationary member 12, sized for introduction into a joint of the body via a puncture opening through the flesh, and a rotatable inner member 14 coaxial with the outer member and defining a distal shearing element 16 exposed through a distal opening 18 in the side and end surfaces of the outer member. Disposed along each side edge of the aperture 18 are table extensions 20, seen most clearly in FIGS. 1 and 2, which project outwardly from the body of the outer stationary member, defining retrograde table surfaces 22 that extend beyond a blade surface 23 provided by the projection of thickness, T, of the wall of the outer member, and forming a generally concave opening into the instrument.

Referring to FIG. 2, the proximal end of instrument 10 is received in powered handpiece 24, e.g., a component of the Universal Surgical System sold by Dyonics, Inc. of Andover, Mass., as described by Sjostrom et al. in U.S.S.N. 693,779, which is incorporated herein by reference. The handpiece 24 is connected proximally to a source of suction 26, which draws a vacuum through a conduit defined through the handpiece 24 and instrument 10, to aperture 18. The aperture provides communication between the interior conduit defined through the instrument and handpiece, and the environment about distal end of the instrument, the vacuum created by suction source 26 within the conduit tending to draw uncut tissues into aperture 18, and also evacuating, e.g., particles of tissue removed by instrument 10, as described below.

The proximal end of rotatable inner member 14 is associated with a reversible rotational drive motor disposed within handpiece 24. A controller/power source 28, connected via cable 30, powers the drive motor in handpiece 14 at a maximum rate of up to about 1400 rpm, and foot control 32 allows the surgeon to actuate the instrument to rotate in either direction, with his foot, leaving his hands free.

Figure 4:
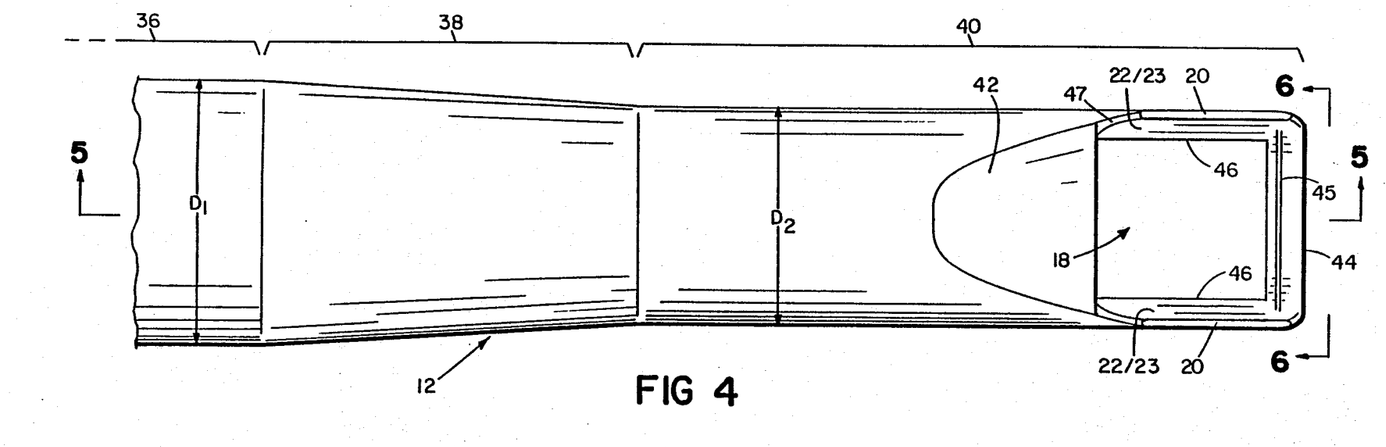
Figure 5:
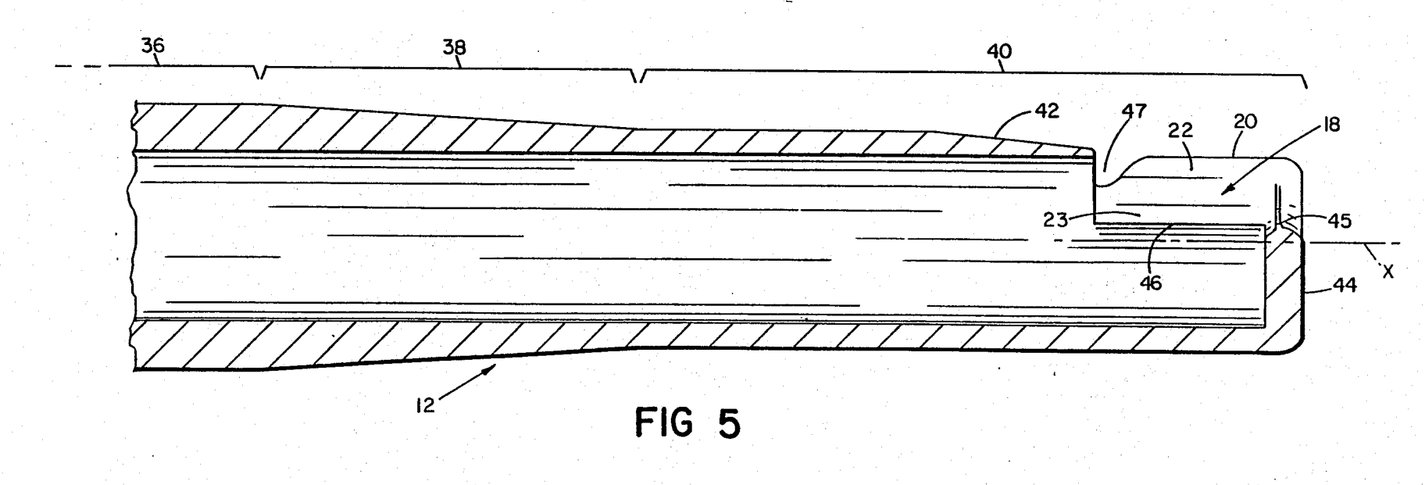
FIG. 5 is a side section view thereof, taken at the line 5—5 of Fig, 4.
Figure 6:
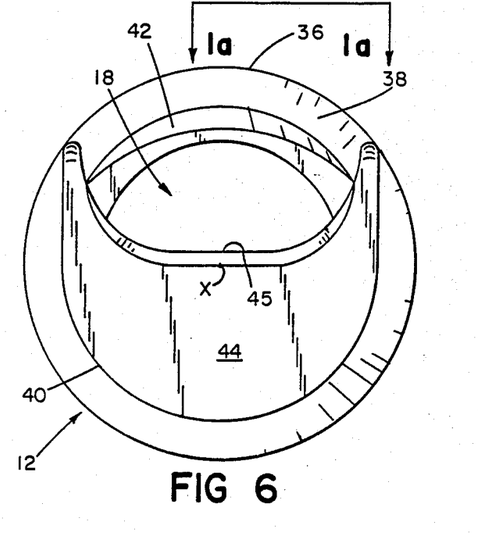
FIG. 6 is an end view thereof, taken at the line 6—6 of FIG. 4.

Referring to FIGS. 4 and 5, the tubular, outer stationary member 12 includes a first, generally cylindrical proximal portion 36 of substantially uniform outer diameter, $D_1$, e.g., 5.5 mm, or, for use in the region of the posterior horn of the meniscus, 4.0 mm. Distal of cylindrical portion 36 lies a frustoconical portion 38 having a decreasing outer diameter in the distal direction, to diameter, $D_2$, of the distal segment 40 of the instrument, which, being less than diameter, $D_1$, facilitates manuveuring and positioning of the distal end of the instrument within the confines of a joint. Removal of tissue from within the joint is further facilitated by a flattening of the surface of the outer member immediately proximal of the aperture 18 to form a flat, sloping surface 42 that, in combination with the end surface opening defined by the crescent shape distal end surface 44 defining distal end cutting edge 45 (FIG. 6), improves access of the cutting aperture of the instrument to tissue to be cut, as will be described below.

The inner surface of the outer member 12 at aperture 18 defines a pair of axially-extending first, fixed cutting edges 46 at opposite sides of the aperture 18, adapted to coact with the cutting edges of cutting element 16 of rotatable inner member 14, which we describe below with reference to FIGS. 7-9. Table extensions 20, defining retrograde table extension surfaces 22, project generally outwardly from the body of the outer member 12 from the blade surfaces 23 at the first, fixed cutting edges 46, as best seen in FIGS. 1 and 10, by a distance, S, which is at least 20% of the thickness, T, of the sidewall of the outer member. The extension and blade surfaces at the sides of the aperture, in combination, define a substantially concave opening to aperture 18. Immediately proximal of each table extension 20 there is defined a notch 47 in the region of the intersection of the outer member 12 and the proximal ends of the extensions, the purpose of which will be described below. There is thus provided an outer member of construction providing maximum accessibility, in a limited space, to a tissue-shearing aperture, a particular advantage in removing relatively firm tissue at higher speeds of rotation, when the shearing behavior of the inner movable member approaches that of a smooth cylinder.

Figure 1A:
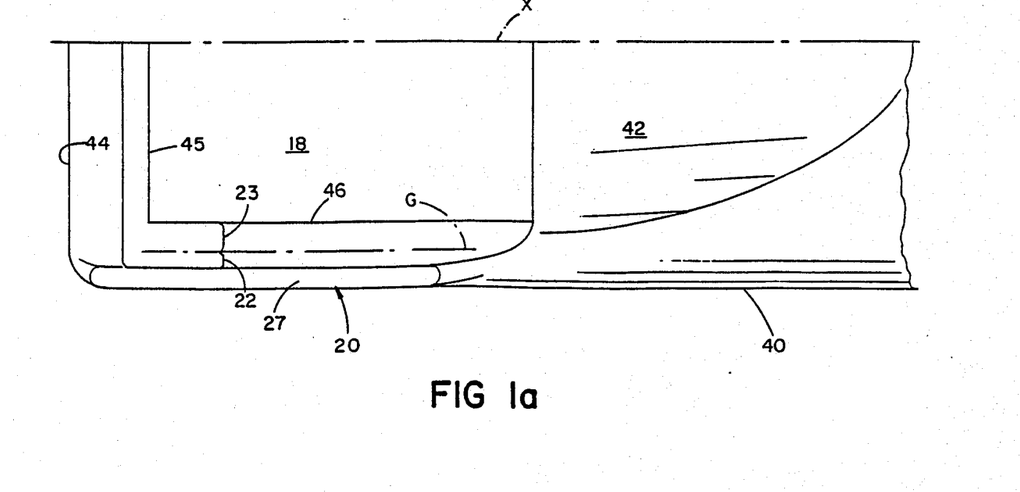
FIG. 1a is a partial plan view of the outer member taken at the line 1a—1a of FIG. 6.

The retrograde extension surfaces defined by table extensions 20 serve to increase the size of the tissue-receiving window offered by the instrument, as the extensions act to capture and immobilize tissue in the area of the coacting cutting edges 46, 66 for enhanced cutting of a variety of character of tissue encountered, e.g., in the knee. Referring to FIGS. 1 and 1a, the table extension 20 extends outwardly beyond a projection, Y, of the outer surface 25 of the outer member 12, preferably by a distance, S, measured along a radius, R, about the axis of rotation, X, of the inner member, drawn through the first cutting edge 46. (As mentioned above, S is at least 20% of the general side wall thickness, and preferably is significantly greater than 20%, as shown, within other parameters described herein.) The angle, A, of the table extension surface 22 to the radius, R, through the first cutting point 46, is greater than the angle, B, of the edge surface 23, causing the combined retrograde surface to have a component of projection, P, in the direction opposed to the direction of cutting movement, C, of the inner member 14, and providing a total immobilizing surface of area approximately double that of the edge surface alone. This retrograde relationship is further indicated by dimension, J, a projection from the radius, R', through point G at the intersection of blade surface 23 and extension surface 22. The concave shape of the combined surfaces 22, 23 further serves to enhance the definition of first cutting edge 46. Each table extension 20 extends outwardly to terminate in a distal surface 27 lying at or beyond a line, D, projected tangent to the path of the second cutting edge 66 of inner member 14 at its midpoint, E, between the first cutting edges 46.

Each table extension 20 has an outer surface 29 which is a continuation of the outer surface 25 of the outer member 12. The outer surfaces 29 lie on, or within, parallel planes $F_1$, $F_2$, projected tangent to the opposite sides of the outer member, whereby the critical diameter, $D_2$, of the surgical instrument is not increased by the table extensions, and the instrument may be introduced into the narrow space between the femoral condyl and the tibial plateau, as described below with reference to FIG. 11.

The rotatable cutter element 14 is a tube having a partially closed end, with an asymmetrical cutting arrangement defined in a distal region 16. Cutting edges 48, 50 are defined about openings 52, 54 on opposite sides of the inner element and extend into the distal end surface 56. Each cutting edge consists of a proximal, first circular opening portion 58, 59, formed, e.g., with ball cutters, through the side wall of the tubular inner element 14, generally into its interior, and a distal second, semicircular opening portion 60, 61, in the side wall of the inner element, and extending hemispherically into the end wall 56 of the element. The radii of the respective distal openings extend proximally to overlap the adjacent respective proximal openings, and extend distally, beyond the end surface of the cutting element. The axes ($A_p$, $A_p'$, $A_D$, $A_D'$) of the pairs of proximal and distal opening portions are longitudinally staggered from one another in order to provide a region having asymmetrical cutting action with cutting points 62, 64, 66 that are offset longitudinally from each other, and also to provide the body of element 14 with nearly constant transverse cross sectional area along the distal region 16 of the second cutting edges 48, 50. Element 14 is thus able to better withstand the relatively high stresses associated with the shearing of thick tissue. The longitudinally staggered cutting point arrangement also serves to minimize the risk found with other arthroscopic cutters using a rotating cutting blades having aggressive cutting tendencies, i.e., of winding tissue about the blade, dragging healthy tissue into the instrument, and provides better performance in cutting soft, slippery tissue.

The body of cutter element 14 in the cutting region 16, between cutting edges, is tapered distally so that the aperture 18 remains open at nearly all rotational positions of the inner element 14 to perpetually draw target tissue toward the instrument 10 for cutting and sculpting. Referring to FIG. 10, crescent-shaped scallops 68, 70, defined by the distal end surface 56 of inner element 14, define end cutting edges adapted, in cooperation with outer member distal end cutting edge 45, to cut tissue approached from the distal end of the instrument. Scallops 68, 70 serve to produce a smooth, transitional joint surface between sections of tissue removed by distal end cutting and sections removed by side cutting, thus having the highly desirable effect of producing a smooth, low friction joint surface upon which the surrounding bones may articulate.

Figure 8:
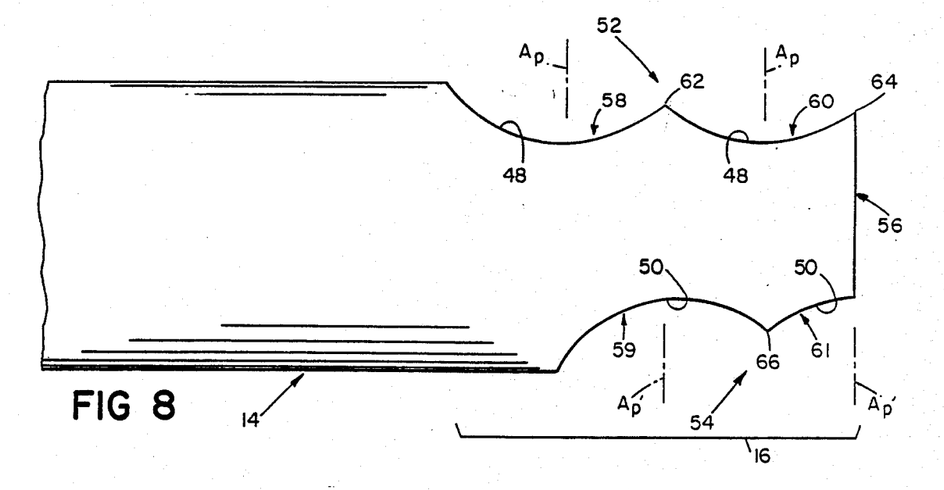
FIG. 8 is a side view and FIG. 9 is a bottom plan view thereof.

Referring to FIG. 10, the rotatable inner element 14 is disposed coaxially with and within outer stationary member 12 (the relationship is shown diagrammatically, with the end wall of the outer member removed for clarity and the inner member sectioned on a plane through points 64, 66, i.e., line 10—10 of FIG. 8). As inner element 14 is rotated, second cutting edges 48, 50 and cutting points 62, 64, 66 coact with the opposed first, fixed cutting edge 46 to shear tissue therebetween, while at the same time, the rotating distal end cutting edges 68, 70 coact with the distal end cutting edge 45 of the outer member to shear tissue extending into the aperture 18 from the distal end of the instrument. (As shown most clearly in FIGS. 1 and 10, the instrument of the invention is constructed for tissue shearing cutting upon rotation of the inner element in either direction of rotation, as selected by the surgeon.)

Figure 11:
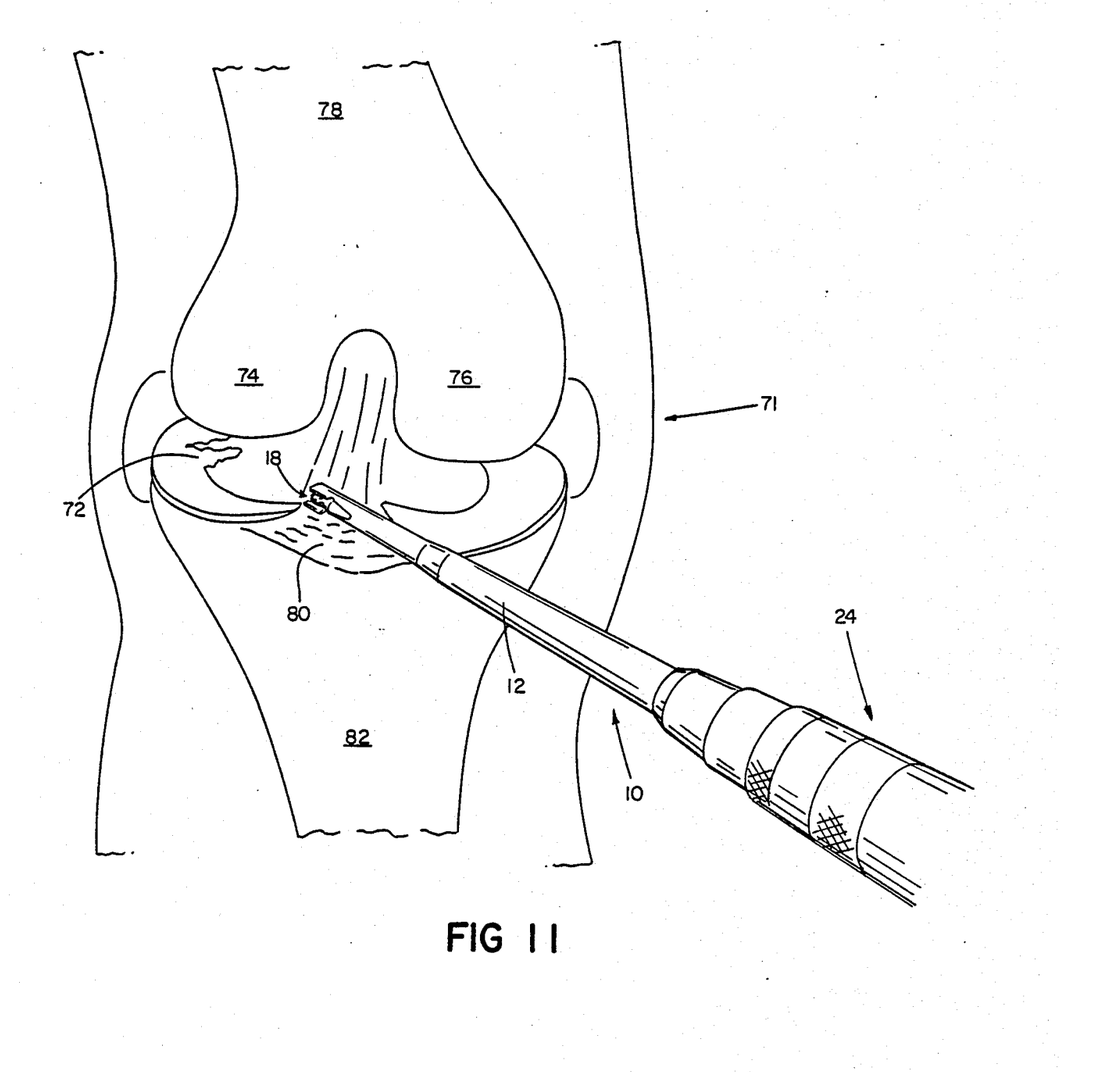
FIG. 11 is a somewhat diagrammatic view of the surgical instrument of the invention being employed for surgery on the meniscal cartilage of the knee.

Referring now to FIG. 11, the distal end of instrument 10 is shown inserted into the joint of knee 71 and positioned for surgical treatment, e.g., by removal of a portion of the menical cartilage 72 lying between condyls 74, 76 of the femur 78 (thigh bone) and the end 80 of the tibia 82 (shin bone). The instrument is critically sized for insertion into the tight confines of the knee joint, with the dimension, $D_2$, of the instrument unaffected by the table extensions, and the outer member 12 has sufficient strength to resist bending when the surgeon applies force to position the cutting end, while permitting easy passage of severed tissue-fragments through the instrument and out of the body.

Typically, during an operative procedure, the patient is given general anesthesia and appropriate punctures of the patient's flesh are made at selected points about the joint by a trocarring cannula. Fluid is introduced into one cannula at a slightly increased pressure to distend the joint, and to provide flow through the joint, through the instrument 10. This substantial volume of flow, e.g., in excess of 100 cc per minute, is provided to ensure that all the tissue severed from the joint is drawn into the instrument and removed from the joint; it also keeps the joint fluid clear for better visual guidance of the instrument, provided via a fiber optic device inserted into the joint through another cannula. The fiber optic device introduces light to the interior of the joint from a light source and returns a visual image along a separate optical path. (The image can be directed to an eye piece for the surgeon, to recording cameras, or to a television camera which creates a display, which the surgeon watches to control his movements.) By watching the screen and manipulating the instrument, the surgeon positions the instrument for removal of tissue.

Figure 12:
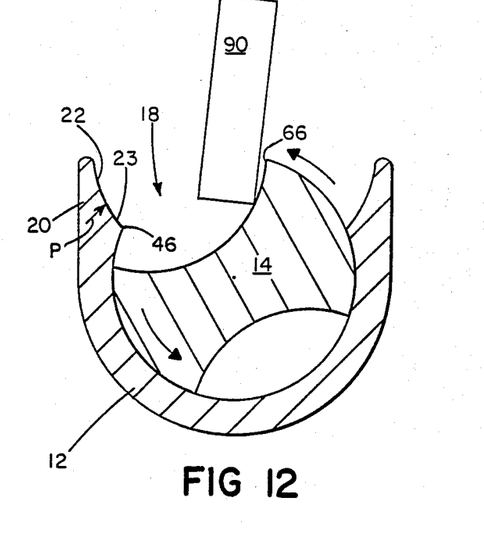
FIGS. 12 through 15 are similarly somewhat diagrammatic views, showing a sequence of tissue removal.

Referring now to FIGS. 12 et seq., the operation of the surgical instrument of the invention for efficient removal of a variety of different tissues will now be described.

Figure 13:
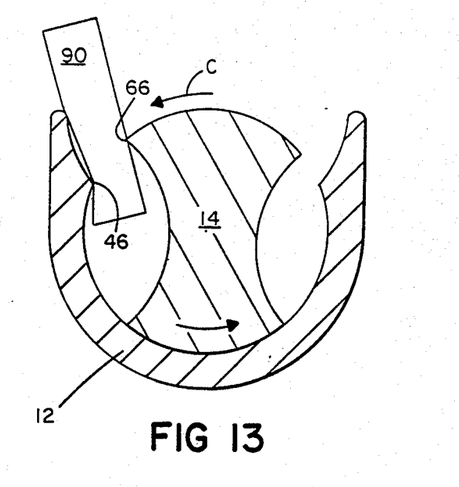
Figure 14:
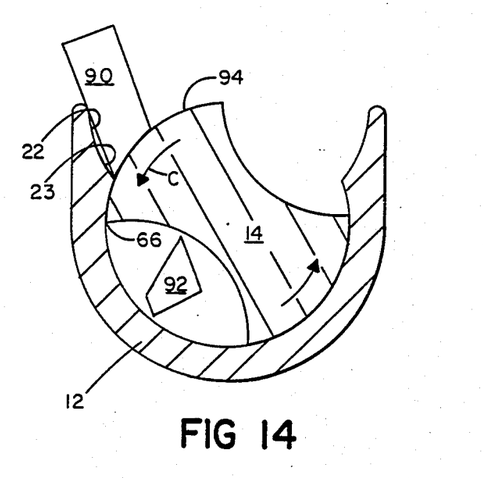
Figure 15:
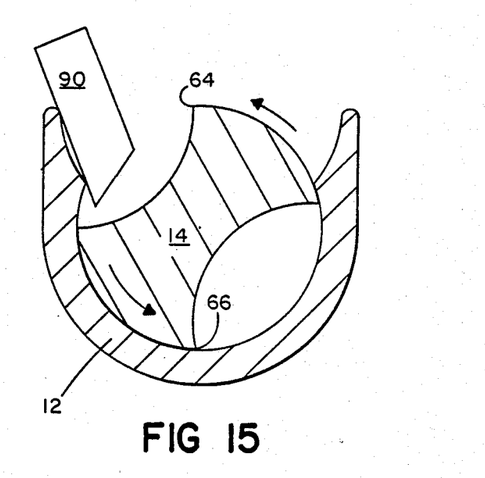

The extension surface 22 of table extension 20, above blade surface 23 and the first fixed cutting edge 46, has a component of projection, arrow P, opposed to the path, arrow C, of the cutting points 62, 64, 66 of the second, cutting edges 48, 50 as they pass the first cutting edge 46 in tissue shearing action. Referring to FIG. 12, tissue, shown representatively by rectangular shape 90, is drawn, by suction from aperture 18 into the path of rotating cutting element 14. In FIG. 13, the second cutting edge 66 has engaged upon the surface of tissue 90 and, by rotation, exerts a drag force upon the tissue toward the shearing nip with fixed edge 46, in a direction substantially normal to immobilizing surface 22. In FIG. 14, the second cutting edge has moved toward and passed closely by the fixed cutting edge to shear a fragment 92 from tissue 90. The fragment 92 is being drawn by suction through the instrument and ultimately out of the body. The remaining portion of the tissue 90 outside the instrument is forced against the immobilizing surface 22 of the table extension. The tissue is thus immobilized and remains in a position (FIG. 15) which allows it to be drawn into the aperture and cut upon a subsequent pass of the cutting edges of element 16. Referring again to FIG. 14, feeding of the uncut tissue portion into the aperture for cutting in subsequent passes of the second cutting edges is further facilitated by the in-feed action of the cylindrical surface 9 of inner cutter element moving past the table surface 22, creating an inrolling nip and urging the tissue into the path of the cutting edge, and by the polished nature of the surfaces 22, 23, which facilitates sliding of the tissue toward the nip.

Powered arthroscopic surgical instruments without immobilizing table extensions typically push or bat tissue away from the instrument, e.g., due to drag and other forces applied to the tissue by the initial cutting action, and as a result produce an irregular series of cuts along the tissue surface rather than creating a smooth, continuous, sculpted surface. Retrograde extensions 20, by immobilizing tissue, permit the instrument 10 to be used for cutting and for tissue sculpting, and allow the surgical procedure to be performed in a markedly shorter period of time, with less trauma for the patient, and the combination of the retrograde table extension with the offset cutting points has been found to offer much improved performance in cutting tissue previously found very difficult to remove with powered instruments, e.g., plica, which is similar in nature to fibrous elastic bands.

Healthy tissue, e.g., in the joint, is typically more firm than unhealthy tissue, which tends to be soft. The extensions 20 of the instrument of the invention are adapted to assist the surgeon to cut aggressively when removing unhealthy, degenerated tissue, and to cut less aggressively when removing healthy tissue, e.g., while sculpting or smoothing the surface of a joint. The instrument of the invention cuts tissue over a wide range of cutting speeds, e.g., from about 100 r.p.m. to 1,000 r.p.m. and above, the speed selected on the basis of tissue encountered. For example, healthy meniscal cartilage about a tear is cut at high speed; partially degenerate cartilage, which is compliant and rubbery, but still retains its form, is most effectively cut at lower speeds; and totally degenerate cartilage and synovial tissue are cut at high speeds.

Figure 7:
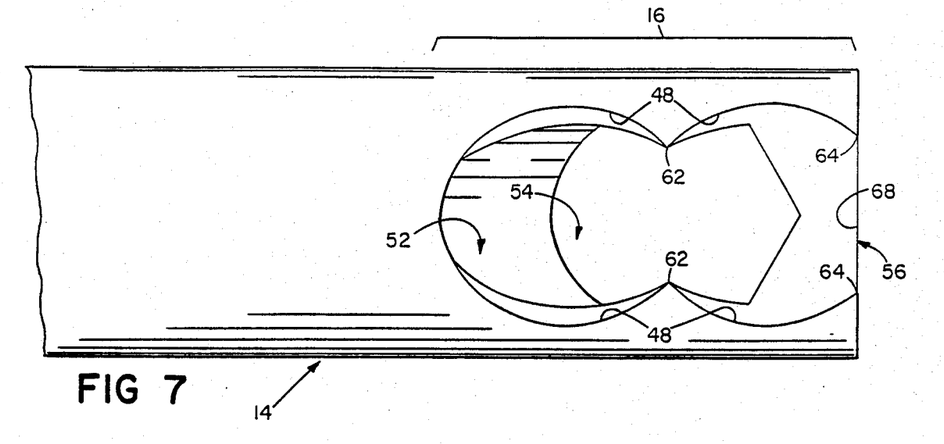
Figure 9:
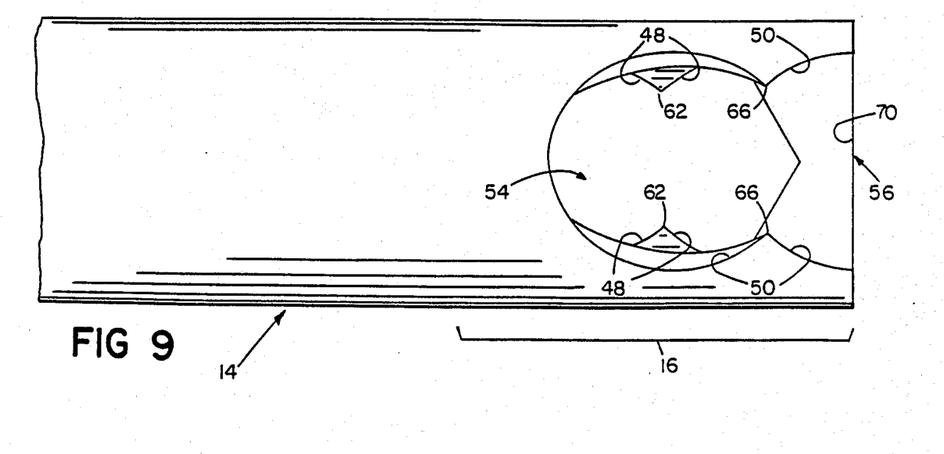
Figure 10:
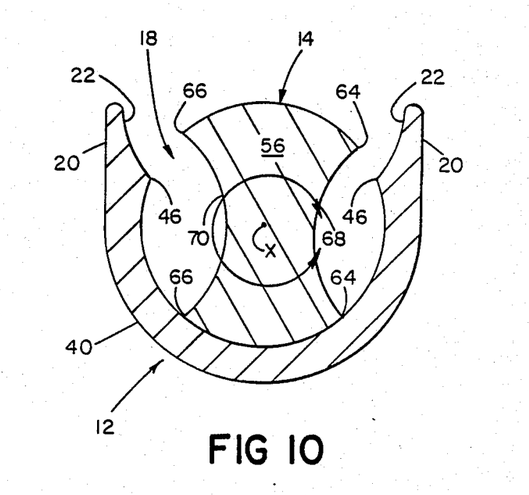
FIG. 10 is a somewhat diagrammatic transverse section of the surgical instrument of the invention, taken at the line 10—10 of FIG. 1.
Figure 16:
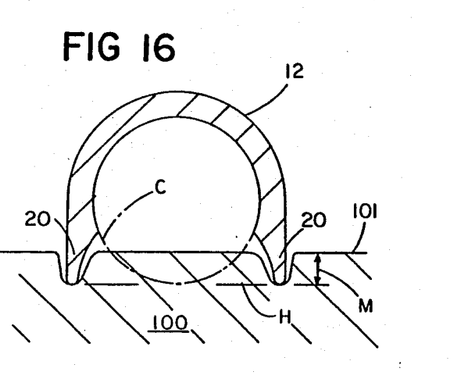
FIGS. 16 through 18, similarly somewhat diagrammatic, show the surgical instrument of the invention engaged for surgery upon surfaces of the joint.
Figure 17:
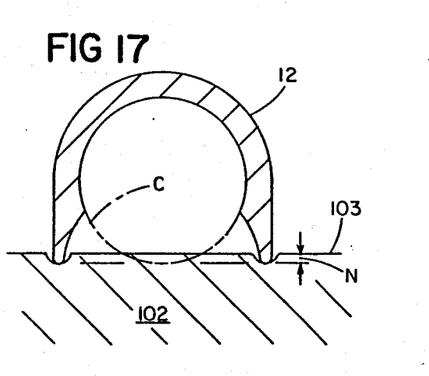

Referring to FIG. 16, the extensions 20 of outer member 12 are arranged relative to the inner cutter member 14, (not shown), so that a line, H, between the outer tips of the extensions lies generally tangent to the path, C, of the cutting points 62, 64, 66 of the second cutting edges 48, 50 (cutting point 62, aligned axially with cutting point 64, is seen in FIGS. 7-9). In FIG. 16, the table extensions 20 are engaged upon a region of generally unhealthy tissue 100, and, because of the softness of the unhealthy tissue, have sunk into the tissue to a depth, M, below the tissue surface 101. The rotating cutting element, with each rotation, penetrates into the tissue to depth, M, removing the soft, unhealthy tissue relatively aggressively. In contrast, in FIG. 17, the table extensions are engaged upon more healthy tissue 102 and sink below the surface 103 only to depth, N, much less than M, and cutting, shaving or scupting, proceeds much less aggressively.

Figure 18:
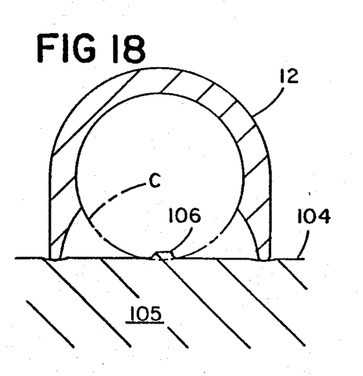

In FIG. 18, the table extensions are engaged upon the surface 104 of relatively hard tissue 105 to provide lateral stability during removal of a nodule or ridge 106 to smooth the surface. Nodules of the type shown typically consist of bone covered by soft tissue. In the past, the surgeon typically removed the soft tissue with a powered blade cutting instrument to expose the bone for removal with an abrading instrument. The exchange of instruments, necessitated by the likelihood of clogging the abrading element if it is used to remove softer tissue, is avoided with the instrument of the invention which removes the soft tissue and bone effectively and in one operation.

Figure 19:
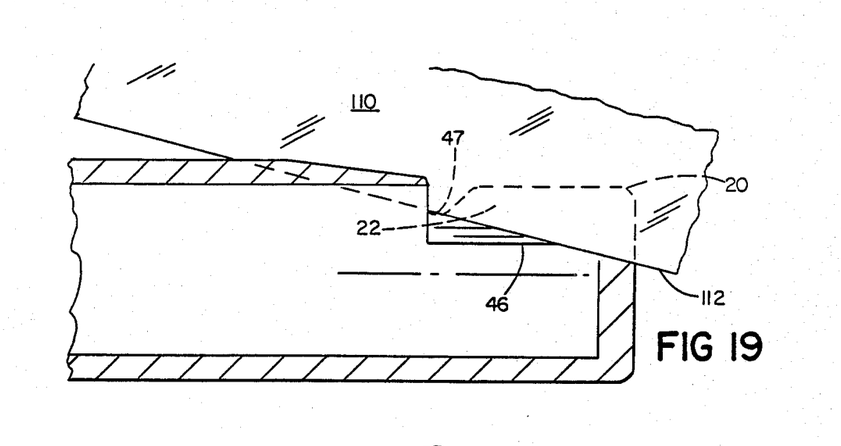
FIG. 19 is a somewhat diagrammatic side section view of the surgical instrument of the invention engaged for cutting tissue along an edge.

Referring to FIG. 19, the cutting instrument 10 of the invention is shown in use for cutting tissue 110 along an edge 112. The instrument is positioned in a manner to engage the edge of the tissue in notch 47 immediately proximal of the table extension 20, and generally against the distal end cutting edge 45 of the instrument. The notch 47 allows the instrument to be positioned for cutting with the instrument axis closer to the edge than would be possible with instruments of other construction, thus providing for smoother and more efficient cutting and sculpting along an edge.

The instrument of the invention thus provides the physician with a single instrument that is adapted to perform debriding and sculpting of tissues within the confines of a human joint in order to reduce the trauma to the surrounding tissues inherent in removing and introducing multiple instruments during a procedure.

Although the present invention has been described with respect to a preferred embodiment, it is understood that a person skilled in the art could make alterations and modifications without departing from the true spirit and scope of the invention. For example, the position of line H relative to line C (FIG. 16) may be adjusted dependent upon the predominant nature of the procedure to be performed, e.g., H may be moved radially outwardly for smoothing osteophytes, or inwardly for more agressive cutting. The table extension may be employed with cutter instruments having inner cutter members of other configurations, e.g., auger or helical blades extending the length of the outer member or joined proximal of aperture 18 to a shaft or inner tube.

The instrument may have a table extension along only one side of the aperture 18. A single table extension could project outwardly to a greater degree than the table extensions of an instrument having extensions at both sides of the aperture while providing an instrument capable of passing through a cannula of the same diameter. Such an instrument would perhaps offer some advantageous features over the preferred instrument described, but at the expense of reduced versatility.

The body of the outer member may have a contour other than cylindrical, e.g., it may be more rectangular. Also, the instrument as shown in the drawing has a flat distal surface 44, but other distal tip end shapes are contemplated, e.g., spherical, bullet-shape, or full-radius.

Figure 20:
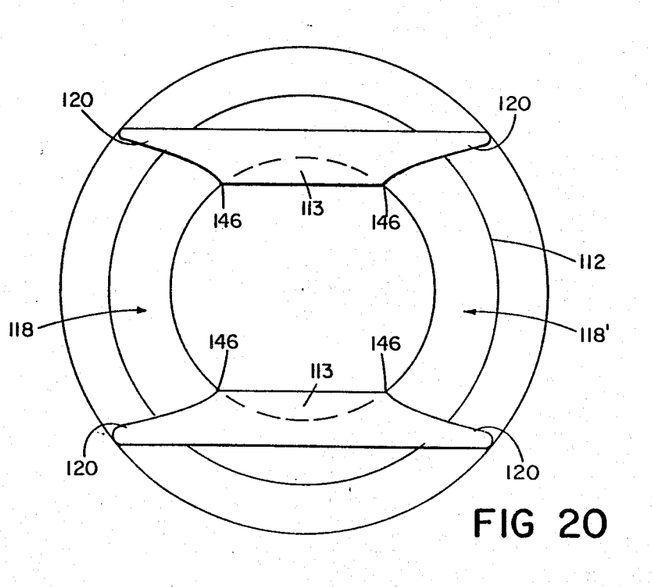
FIGS. 20 and 21 are end and plan views of the distal end of an alternate embodiment of a surgical instrument of the invention.
Figure 21:
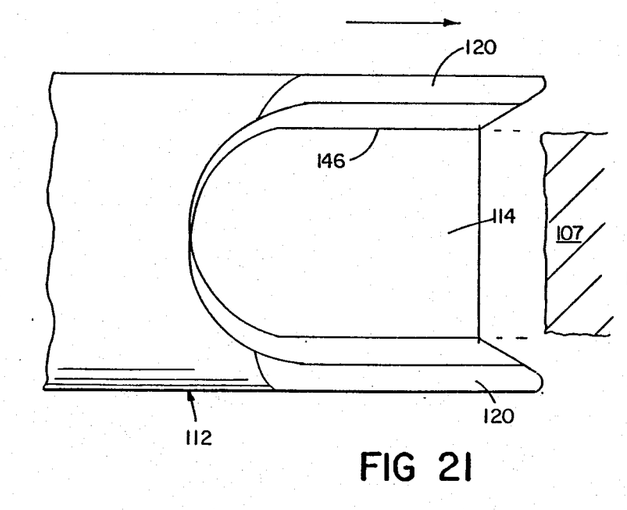

Referring to FIGS. 20 and 21, the cutter instrument especially suited for end on cutting of, e.g., meniscal cartilage 107, may be provided with two apertures 118, 118' on opposite sides of the distal end of the instrument. There may be provided table extensions 120 at one side only of each aperture, e.g., if an auger or other inner member 114 (FIG. 21 only) capable of cutting in only one direction is provided, or with extensions at both sides of each aperture, as shown. (To provide additional strength and effective cutting, the extent of the arcs of the apertures may be reduced, placing the first cutting points 146 closer together, and the distal end portions 113 of the outer member 112 may extend radially inwardly.

I claim:

1. In an arthroscopic surgical instrument comprising an outer stationary member sized to enter a joint through a puncture opening, said outer stationary member comprising a body and defining, in a wall of said body, at least one distal aperture, the wall of the outer member at the aperture defining a first, fixed blade surface terminating in a cutting edge, an internal movable member disposed within the outer member, adapted to be power driven and having a second cutting edge arranged to move toward and closely past said fixed cutting edge in rapid, repetitive fashion to sever tissue, the improvement wherein a table extension at said aperture projects from the body of said outer stationary member in retrograde manner with an outward component and a component that defines a surface opposed to the direction of movement of said second cutting edge and constructed to engage tissue against which the operator urges the instrument, in a manner to improve the repetitive cutting action.

2. The arthroscopic surgical instrument of claim 1 wherein said body is disposed along an axis and said surface of said table extension is disposed parallel to said axis.

3. The arthroscopic surgical instrument of claim 2 or 1 wherein said aperture is defined in a general side wall of said outer member, and said table extension projects from the outer side surface of said outer member in the vicinity of said aperture.

4. The arthroscopic surgical instrument of claim 3 wherein a blade surface that corresponds to the thickness of the general side wall of the outer member lies at a retrograde angle to a radius from the axis of movement of said inner member projected through said first cutting edge and said table extension lies at a greater angle to said radius.

5. The arthroscopic surgical instrument of claim 3 wherein said table extension projects from the outer side surface of said outer member by at least 20% of the thickness of the general side wall of said outer member.

6. The arthroscopic surgical instrument of claim 5 wherein said table extension projects outwardly by at least the order of the thickness of said general side wall.

7. The arthroscopic surgical cutter of claim 6 wherein said table extension projects from the blade surface by at least the order of the thickness of the general side wall of the outer member.

8. The arthroscopic surgical instrument of claim 5 wherein said table extension projects in a retrograde manner from the blade surface by at least 20% of the thickness of the general side wall of the outer member.

9. The arthroscopic surgical cutter of claim 6 wherein said table extension projects from the blade surface by at least the order of the thickness of the general side wall of the outer member.

10. The arthroscopic surgical instrument of claim 3 wherein said table extension projects outward by at least the order of the thickness of said general side wall.

11. The arthroscopic surgical cutter of claim 10 wherein said table extension projects from the blade surface by at least the order of the thickness of the general side wall of the outer member.

12. The arthroscopic surgical instrument of claim 3 wherein said table extension projects in a retrograde manner from the blade surface by at least 20% of the thickness of the general side wall of the outer member.

13. The arthroscopic surgical cutter of claim 12 wherein said table extension projects from the blade surface by at least the order of the thickness of the general side wall of the outer member.

14. The arthroscopic surgical instrument of claim 2 wherein said outer member comprises a tube having a generally cylindrical form,.

15. The arthroscopic surgical instrument of claim 2 wherein said table extension defines a tissue immobilizing surface.

* * * * *

UNITED STATES PATENT AND TRADEMARK OFFICE
CERTIFICATE OF CORRECTION

PATENT NO. : 4,983,179

DATED : January 8, 1991

INVENTOR(S) : Douglas D. Sjostrom

It is certified that error appears in the above-identified patent and that said Letters Patent is hereby corrected as shown below:

Col. line 4, replace "division" with --continuation--.

Col. 2, line 68, delete "instrument" (2nd occurrence).

Col. 3, line 15, replace "Point" with --point--.

Col. 3, line 24, replace "assymetric" with --asymmetric--.

Col. 3, line 31, before "resections" insert --debridement, synovial resection, removal of osteophytes, plica--.

Col. 3, lines 32-33 delete "debridement, synovial resection, removal of osteophytes, plica".

Col. 3, line 53, replace "Power" with --power--.

Col. 7, line 68, replace "9" with --94--.

Signed and Sealed this

Second Day of February, 1993

Attest:

STEPHEN G. KUNIN

Attesting Officer     Acting Commissioner of Patents and Trademarks